US006646177B2

(12) United States Patent
Takahashi et al.

(10) Patent No.: US 6,646,177 B2
(45) Date of Patent: Nov. 11, 2003

(54) METHOD FOR SEPARATION OF P-XYLENE

(75) Inventors: Tomonori Takahashi, Nagoya (JP); Hitoshi Sakai, Nagoya (JP); Naoyuki Ogawa, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/929,385

(22) Filed: Aug. 14, 2001

(65) Prior Publication Data
US 2002/0045792 A1 Apr. 18, 2002

(30) Foreign Application Priority Data
Aug. 23, 2000 (JP) ........................ 2000-252578

(51) Int. Cl.[7] ................ C07C 7/144; B01D 53/22; B01D 61/00
(52) U.S. Cl. ................ 585/818; 585/819; 585/820; 210/651; 210/653; 95/45; 95/50
(58) Field of Search ................ 585/818, 819, 585/820; 210/651, 653; 95/45, 50

(56) References Cited
U.S. PATENT DOCUMENTS
5,942,119 A    8/1999   Deckman et al. ........... 210/651

FOREIGN PATENT DOCUMENTS

| JP | 60-028826 | 2/1985 |
| WO | 93/17781 | 9/1993 |
| WO | 94/25151 | 11/1994 |

*Primary Examiner*—Walter D. Griffin
*Assistant Examiner*—Tam M. Nguyen
(74) *Attorney, Agent, or Firm*—Burr & Brown

(57) ABSTRACT

A method for separating p-xylene by separating and recovering only p-xylene from a p-xylene-containing raw material mixture under high-temperature and high-pressure conditions using a zeolite membrane as a separating membrane is provided. The p-xylene partial pressure at the raw material side of the separating membrane is kept at a sufficiently high pressure and the p-xylene partial pressure at the recovery side of the separating membrane is controlled at a pressure which is not higher than the inflection point of p-xylene adsorption curve. This method for separating p-xylene using a zeolite membrane as a separating membrane can secure a sufficient p-xylene permeation amount and has industrial applicability.

6 Claims, 2 Drawing Sheets

METHOD FOR SEPARATION OF P-XYLENE

BACKGROUND OF THE INVENTION AND RELATED ART STATEMENT

The present invention relates to a method for separating p-xylene by separating and recovering only p-xylene from a p-xylene-containing raw material mixture. More particularly, the present invention relates to a method for separating p-xylene using a zeolite membrane as a separating membrane.

Xylene (dimethylbenzene) has three isomers (o-xylene, m-xylene and p-xylene) depending upon the positions of two methyl groups. Among the three isomers, p-xylene (which is a 1,4-substitution product of benzene) is particularly important because it, when oxidized, becomes terephthalic acid which is industrially useful as a starting material for polyesters such as PET, PBT and the like.

p-Xylene, together with o-xylene, m-xylene and ethylbenzene, is present in, for example, the C-8 fraction of coal tar. Since these compounds have the same molecular weight and are close in boiling point, it is impossible to separate p-xylene from their mixture by fractional distillation alone. Therefore, methods are under study which comprise separating and recovering only p-xylene from a raw material mixture using, as a separating membrane, a membrane composed of zeolite known as a molecular sieve.

For example, JP-B-5-63410 discloses a method for separating only p-xylene selectively from a m-xylene/p-xylene mixture using a ZSM-5 (MFI) type zeolite membrane formed, in a thin film, on a porous glass (a substrate). This method is hereinafter referred to as "the first method."

Also, WO 93/17781 discloses a method for separating only p-xylene selectively from an equal volume mixture of m-xylene, p-xylene and triisopropylbenzene using a ZSM-5 (MFI) type zeolite membrane under the conditions of room temperature and a total pressure (at raw material side) of 1,720 kPa (p-xylene partial pressure=573 kPa). This method is hereinafter referred to as "the second method."

Further, WO 94/25151 discloses a method for separating only p-xylene selectively from a o-xylene/p-xylene mixture using a MFI type zeolite membrane under the conditions of 100 to 200° C. and a p-xylene partial pressure (at raw material side) of 0.31 kPa. This method is hereinafter referred to as "the third method."

The above separation methods are useful in that they can separate p-xylene selectively; however, they have a problem in that the amount of p-xylene permeating through the zeolite membrane is small. Hereinafter, the amount is referred to as "p-xylene permeation amount."

In order to make the separation of p-xylene using zeolite industrially applicable, it is necessary to separate and recover a large amount of p-xylene efficiently (so as to match the cost and equipment used) under the high-temperature and high-pressure conditions of 200° C. or higher and 25 kPa or higher (a p-xylene partial pressure at the raw material side); that is, a large p-xylene permeation amount is required. However, none of the above methods are fully satisfactory in providing a large p-xylene permeation amount.

The second method is a method for separating p-xylene at a low temperature (room temperature); the third method is a method for separating p-xylene at a low pressure (the p-xylene partial pressure at raw material side is 0.31 kPa); and the first method makes no mention at all about separation conditions or p-xylene permeation amount and therefore shows no study based on p-xylene permeation amount.

Thus, as to a method for separation of p-xylene using a zeolite membrane, there is no industrial application yet.

SUMMARY OF THE INVENTION

In view of the above-mentioned problems of the prior art, the present invention is intended to provide a method for separating p-xylene, which can secure a sufficient p-xylene permeation amount and has industrial applicability.

The present inventors made an in-depth study on p-xylene adsorption on zeolite under a high temperature condition, in order to obtain an increased p-xylene permeation amount. As a result, the present inventors surprisingly found out a fact that at a low p-xylene partial pressure region, the p-xylene adsorption increases sharply with an increase in p-xylene partial pressure, but the increase becomes strikingly small when the p-xylene partial pressure is at a certain level or larger. The present invention has been completed based on the above finding.

According to the present invention, there is provided a method for separating p-xylene, which comprises separating and recovering only p-xylene from a p-xylene-containing raw material mixture under high-temperature and high-pressure conditions using a zeolite membrane as a separating membrane, in which method the p-xylene partial pressure at the raw material side of the separating membrane is kept at a sufficiently high pressure and the p-xylene partial pressure at the recovery side of the separating membrane is controlled at a pressure which is not higher than the inflection point of a p-xylene adsorption curve.

In the separation method of the present invention, the p-xylene partial pressure at the raw material side of the separating membrane is controlled preferably at a pressure higher than the inflection point of a p-xylene adsorption curve; it is preferred that the separation is conducted at 200° C. or higher, the p-xylene partial pressure at the raw materials side of the separating membrane is kept at 100 kPa or higher, and the p-xylene partial pressure at the recovery side of the separating membrane is controlled at 20 kPa or lower; and the separating membrane is preferably a zeolite membrane composed of a MFI type zeolite.

In the separation method of the present invention, the p-xylene partial pressure at the raw material side of the separating membrane is kept at a sufficiently high pressure and the p-xylene partial pressure at the recovery side of the separating membrane is controlled at a pressure which is not higher than the inflection point of p-xylene adsorption curve. Therefore, the present separation method can secure a sufficient p-xylene permeation amount and has industrial applicability.

DETAILED DESCRIPTION OF THE INVENTION

The separation method of the present invention is described in detail below.

The separation method of the present invention is based on the new finding by the present inventors that at a low p-xylene partial pressure region, the p-xylene adsorption increases sharply with an increase in p-xylene partial pressure, but the increase of the p-xylene adsorption becomes strikingly small when the p-xylene partial pressure is at a certain level or larger.

Figure 1A:
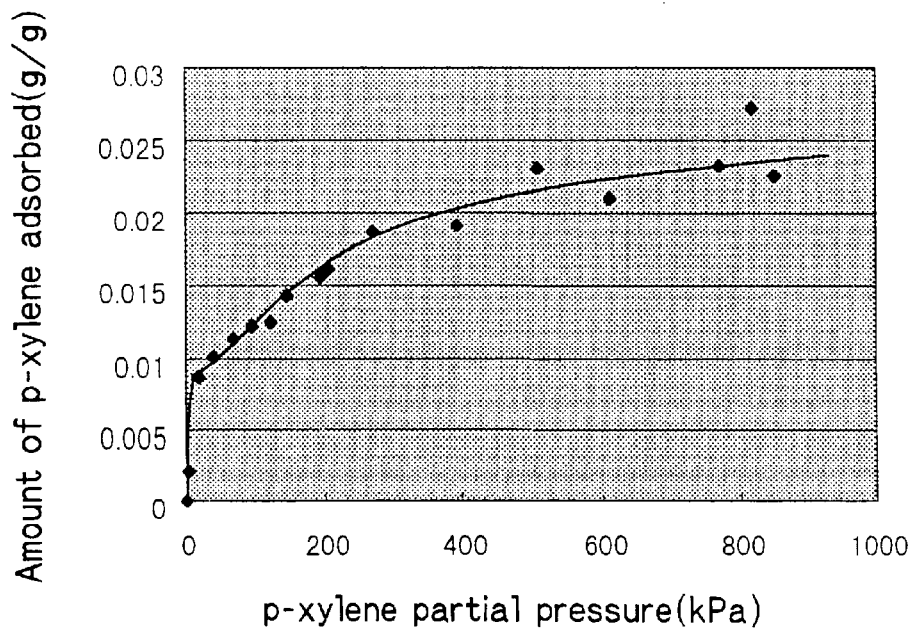
FIG. 1(*a*) is a graph of a p-xylene adsorption curve showing the relationship between p-xylene partial pressure and p-xylene adsorption amount, and FIG. 1(*b*) is a graph wherein the low-pressure part of the FIG. 1(*a*) graph is enlarged.
Figure 1B:
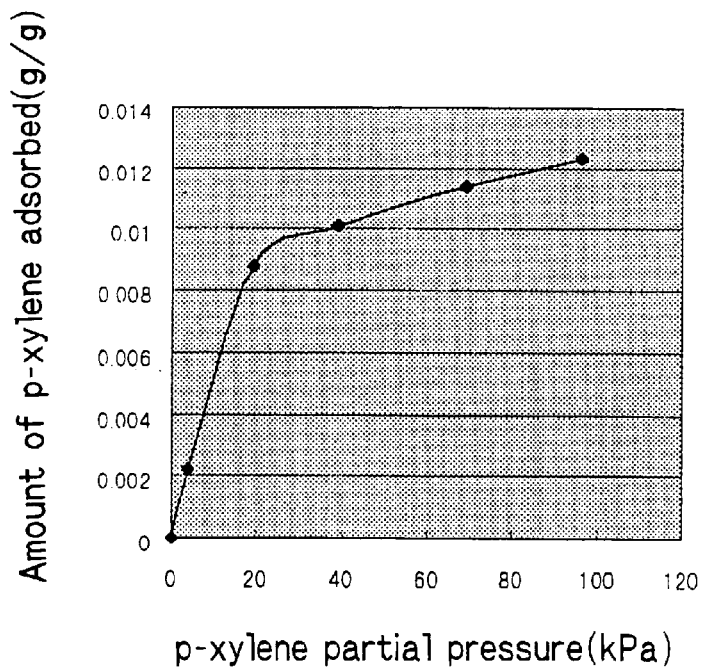

FIGS. 1(a) and 1(b) are graphs of a p-xylene adsorption curve at 400° C., obtained by the measurement by the present inventors, and show the relationship between the partial pressure of p-xylene and the amount of p-xylene adsorption on the surface or its vicinity of a separating membrane composed of zeolite.

As is clear from FIGS. 1(a) and 1(b), the p-xylene adsorption amount increases sharply with an increase in p-xylene partial pressure, at a p-xylene partial pressure region of 20 kPa or smaller, but the increase of the p-xylene adsorption amount becomes strikingly small at a region of 100 kPa or larger. Therefore, at a temperature condition of 400° C., a p-xylene partial pressure of 20 kPa corresponds to the "inflection point" referred to in the present invention.

Meanwhile, as shown by the following formula (1), the amount J of p-xylene permeating through a separating membrane is determined by a difference between (1) the amount Am of p-xylene adsorbed on the surface or its vicinity of the raw material side of separating membrane and (2) the amount Ap of p-xylene adsorbed on the surface or its vicinity of the recovery side of separating membrane, and it is presumed that there is a linear relationship between the above difference in adsorption amount and the permeation amount J. (wherein J is a p-xylene permeation amount; K is a proportional factor; Am is an amount of p-xylene adsorbed on the surface or its vicinity of the raw material side of separating membrane; and Ap is an amount of p-xylene adsorbed on the surface or its vicinity of the recovery side of separating membrane).

As shown in FIGS. 1(a) and 1(b), the amount of p-xylene adsorbed increases dependently with an increase in p-xylene partial pressure; therefore, by controlling the p-xylene partial pressure Pm at the raw material side of separating membrane so as to become higher than the p-xylene partial pressure Pp of the recovery side of separating membrane, a difference arises between the p-xylene adsorption amount Am at the raw material side and the p-xylene adsorption amount Ap at the recovery side and p-xylene permeates through the separating membrane from the raw material side to the recovery side.

In this case, when the p-xylene partial pressure Pp at the recovery side is set at a level not higher than the inflection point (at this level, the increase in p-xylene adsorption amount is large), the difference between the p-xylene adsorption amount Am at the raw materials side and the p-xylene adsorption amount Ap at the recovery side is large and the permeation amount of p-xylene can be increased efficiently.

It is necessary that the p-xylene partial pressure Pm at the raw materials side is controlled at a pressure higher than the p-xylene partial pressure Pp at the recovery side and further is kept at a sufficiently high pressure in order to make large the difference between the p-xylene adsorption amount Am at the raw material side and the p-xylene adsorption amount Ap at the recovery side and secure a large p-xylene permeation amount. Therefore, the p-xylene partial pressure Pm at the raw materials side is preferably controlled at a level higher than the inflection point of p-xylene adsorption curve.

Specifically, the p-xylene partial pressure Pm at the raw material side is necessarily at least 25 kPa, preferably at least 50 kPa, particularly preferably at least 100 kPa.

FIGS. 1(a) and 1(b) show a p-xylene adsorption curve at 400° C. An inflection point such as seen in FIGS. 1(a) and 1(b) is present as well in p-xylene adsorption curves at other temperatures. At temperatures lower than 400° C., the inflection point is at a pressure lower than that at 400° C. and, at temperatures higher than 400° C., the inflection point is at a pressure higher than that at 400° C.

Therefore, the effect of the present invention can be obtained also at a desired temperature other than 400° C., by preparing a p-xylene adsorption curve at that desired temperature to examine an inflection point at that temperature, controlling the p-xylene partial pressure at the recovery side at a level hot higher than the inflection point, and conducting p-xylene separation in this state.

Thus, in the separation method of the present invention, an optimum p-xylene partial pressure suited for the separation temperature selected can be set, and a high p-xylene permeation amount can be secured efficiently.

The temperature at which p-xylene separation is conducted need be not lower than at least 200° C. in order to obtain a sufficient p-xylene permeation amount.

The C-8 residual gas after p-xylene separation is partially converted into p-xylene at a high temperature and reused in p-xylene separation. Also in relation to this high temperature for conversion, the p-xylene separation temperature is preferably not lower than 200° C.

There is no particular restriction as to the upper limit of the p-xylene separation temperature. The upper limit can be appropriately set in view of the p-xylene selectivity in separation or the energy amount required.

In view of the above matters, it is particularly preferred in the present invention to use a separation temperature of not lower than 200° C., keep the p-xylene partial pressure of the raw material side of separating membrane at 100 kPa or higher, and control the p-xylene partial pressure of the recovery side of separating membrane at 20 kPa or lower.

In order to control the p-xylene partial pressure of the recovery side at a level not higher than the inflection point, there can be used, for example, a method of making vacuum the recovery side by a vacuum pump, or a method of introducing a sweep gas (e.g. a diluting gas) into the recovery side. In these methods, the recovered p-xylene gas is quickly discharged out of the separation system, whereby the p-xylene partial pressure at the recovery side can be lowered correspondingly.

There is no particular restriction as to the kind of the sweep gas used; however, a gas non-reactive to p-xylene, such as $N_2$ gas or the like can be used preferably.

The separating membrane used in the present separation method has no particular restriction as to the structure, shape, etc. as long as it is composed of zeolite. However, in order to lower the pressure loss inside the separating membrane, there is preferred a separating membrane obtained by forming a thin zeolite membrane on a porous substrate high in porosity and large in pore diameter. The kind of zeolite composing the separating membrane is preferably, for example, a MFI type zeolite.

When there is used a separating membrane obtained by forming a thin zeolite membrane on a substrate, such as mentioned above, the separating membrane is preferably placed so that the substrate is positioned at the raw materials side and the zeolite membrane is positioned at the recovery side.

The reason for the above placement is as follows. When the substrate is positioned at the recovery side, it is necessary to estimate the actual p-xylene partial pressure at the recovery side of separating membrane by adding the pressure loss of the substrate (this is inconvenient); further, when a sweep gas is used, the mutual diffusion of p-xylene and the sweep gas in the substrate becomes a resistance and thereby the actual p-xylene partial pressure at the recovery side of separating membrane becomes, in some cases, even higher than when influenced by the pressure loss of the substrate.

Next, the present invention is described in detail by way of Examples. However, the present invention is in no way restricted by these Examples.

In the following Examples, there was produced a self-supporting, sheet-like zeolite membrane composed of MFI type zeolite, having an apparent thickness of 60 μm. A ground material of the zeolite membrane was used for measurement of p-xylene adsorption amount, and the zeolite membrane itself was used for measurement of p-xylene permeation amount.

The above sheet-like zeolite membrane was produced by, in an autoclave, forming a membrane on a teflon sheet from a sol composed of $SiO_2$:TPAOH:TPABr:$H_2O$ = 1:0.25:0.25:125 and then removing the teflon sheet. The membrane formation was conducted at 180° C. for 24 hours. Incidentally, "TPA" refers to tetrapropylammonium.

Using the ground material of the zeolite membrane, there was examined a relationship between the p-xylene partial pressure and the amount of p-xylene adsorbed on the zeolite ground material. A balance was held via magnetism in a vessel resistant to high temperatures and high pressures. On this balance was placed the zeolite ground material. Into the vessel was introduced p-xylene gas at 400° C., and there was measured a change in weight, that is, a change in the p-xylene adsorption amount per g of the zeolite ground material, in a p-xylene pressure range of 0 to 850 kPa.

Prior to the above operation, the zeolite ground material was subjected to a pretreatment of keeping the ground material at 500° C. at a vacuum of 0.1 kPa for 12 hours to detach all the components adsorbed thereon.

The result is shown in FIGS. 1(a) and 1(b).

Next, the appropriateness of the following formula (1) was examined experimentally.

The formula (1) is theoretically induced by assuming a diffusion-controlling of p-xylene in separating membrane. Herein, however, p-xylene permeation amounts J were measured using the above-produced separating membrane, at three appropriate combination levels of p-xylene partial pressure Pm at the raw materials side and p-xylene partial pressure Pp at the recovery side, at a separation temperature of 400° C.; From FIGS. 1(a) and 1(b) were read the p-xylene adsorption amounts Am at the raw materials side and the p-xylene adsorption amounts Ap at the recovery side; and there was examined a relationship between (1) the difference between p-xylene adsorption amount Am at the raw materials side and p-xylene adsorption amount Ap at the recovery side and (2) the p-xylene permeation amount J. As the raw material gas for p-xylene separation, there was used $N_2$ gas of 1 atm. containing p-xylene whose partial pressure was the same as the p-xylene partial pressure at the raw material side. The results are shown in Table 1 and FIG. 2.

$$J=K(Am-Ap) \quad (1)$$

(wherein J is a p-xylene permeation amount; K is a proportional factor; Am is an amount of p-xylene adsorbed on the surface or its vicinity of the raw material side of separating membrane; and Ap is an amount of p-xylene adsorbed on the surface or its vicinity of the recovery side of separating membrane).

TABLE 1

| Pm Partial pressure at raw material side (kPa) | Am Adsorption amount at raw material side (mg/g) | Pp Partial pressure at recovery side (kPa) | Ap Adsorption amount at recovery side (mg/g) | J Permeation amount (μmol/(m² · sec)) |
|---|---|---|---|---|
| 0.28 | 0.21 | 0.013 | 0.01 | 2.7 |
| 0.5 | 0.36 | 0.016 | 0.01 | 3.6 |
| 1.01 | 0.69 | 0.036 | 0.03 | 8.1 |

Figure 2:
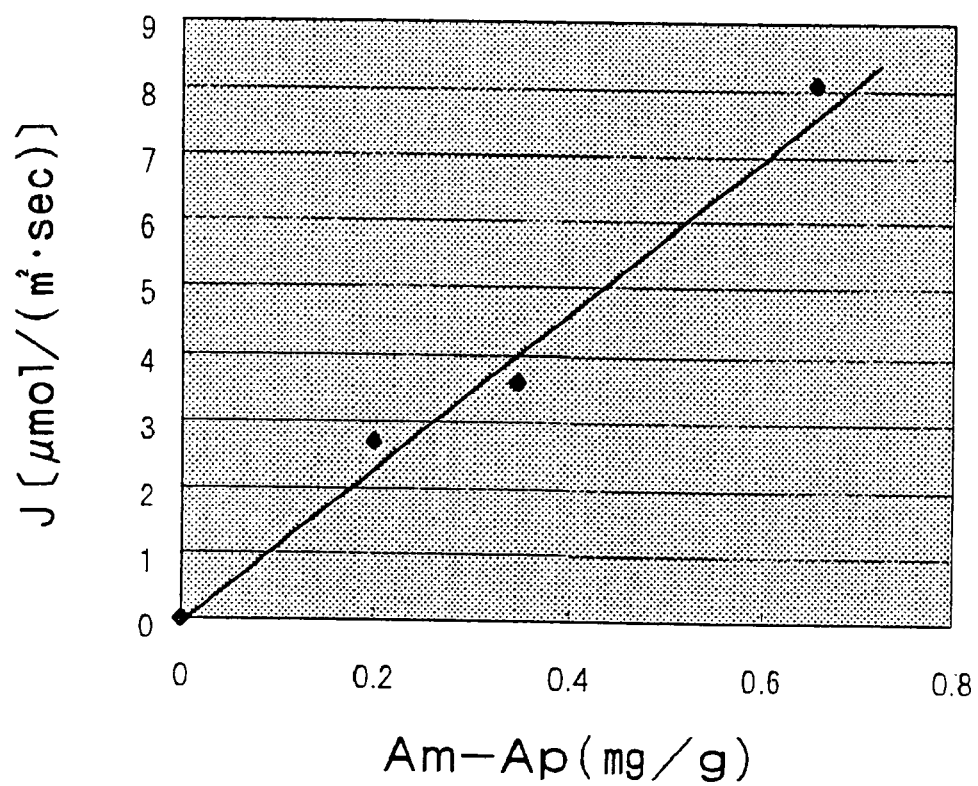
FIG. 2 is a graph showing a relationship of (1) the difference between the p-xylene adsorption amount Am at the raw materials side and the p-xylene adsorption amount Ap at the recovery side and (2) the p-xylene permeation amount J in a separating membrane composed of zeolite.

As is clear from FIG. 2, p-xylene permeation amount J increased dependently upon the difference between p-xylene adsorption amount Am at the raw materials side and p-xylene adsorption amount Ap at the recovery side, and they were in a nearly linear relationship.

Thus, the appropriateness of the formula (1) was proven from the results of the above experiment.

Incidentally, the proportional factor K was 12.3 μmol/(m²·sec)(mg/g).

Using the formula (1) whose appropriateness was experimentally proven as above and the relationship of FIGS. 1(a)(b) between p-xylene partial pressure and amount of p-xylene adsorbed on zeolite ground material, simulation was conducted for p-xylene permeation amounts when the partial pressure of p-xylene was varied very largely. The results are shown in Table 2.

TABLE 2

[0047]

| | Pm Partial pressure at raw material side (kPa) | Am Adsorption amount at raw material side (mg/g) | Pp Partial pressure at recovery side (kPa) | Ap Adsorption amount at recovery side (mg/g) | K Proportional factor [μmol/(m² · sec) (mg/g)] | J Permeation amount [μmol/(m² · sec)] |
|---|---|---|---|---|---|---|
| Actual measurement | 1.01 | 0.69 | 0.036 | 0.03 | 12.3 | 8.1 |
| Example 1 | 700 | 25 | 1 | 0.68 | 12.3 | 300 |
| Example 2 | 700 | 25 | 10 | 5.5 | 12.3 | 240 |
| Example 3 | 700 | 25 | 20 | 8.8 | 12.3 | 200 |
| Comp. Ex. 1 | 700 | 25 | 100 | 12.6 | 12.3 | 150 |
| Comp. Ex. 2 | 700 | 25 | 200 | 16 | 12.3 | 110 |
| Comp. Ex. 3 | 700 | 25 | 500 | 21 | 12.3 | 50 |
| Example 4 | 620 | 23 | 20 | 8.8 | 12.3 | 175 |

As shown in Table 2, in Comparative Example 1, the p-xylene partial pressure at the raw material side was 700 kPa and the p-xylene partial pressure at the recovery side was 100 kPa which was higher than the inflection point of p-xylene adsorption curve; therefore, the p-xylene permeation amount was only 150 μmol/(m²·sec). In contrast, in Example 3, the p-xylene partial pressure at the raw material side was the same as in Comparative Example 1 but the p-xylene partial pressure at the recovery side was set at 20 kPa which was not higher than the inflection point, whereby the p-xylene permeation amount was increased to a high level of 200 μmol/(m²·sec). In Examples 1 and 2, by controlling the p-xylene partial pressure at the recovery side at a low level and making sufficiently large the p-xylene partial pressure difference between the raw material side and the recovery side, the p-xylene permeation amounts were increased to even higher levels.

In Example 4, the p-xylene partial pressure at the recovery side was set at 20 kPa (the same as in Example 3) which was lower than the inflection point, and the p-xylene partial pressure difference between the raw materials side and the recovery side was set at 600 kPa which was the same as in Comparative Example 1; however, the p-xylene permeation amount was 175 μmol/(m²·sec) which was larger than in Comparative Example 1 although the p-xylene partial pressure at the raw materials side was lower than in Comparative Example 1; thus, the p-xylene permeation amount was increased efficiently.

As described above, in the separation method of the present invention, the p-xylene partial pressure at the raw material side of the separating membrane is kept sufficiently high and the p-xylene partial pressure at the recovery side of the separating membrane is controlled at a level not higher than the inflection point of p-xylene adsorption curve; thereby, a sufficient p-xylene permeation amount can be secured and the present separation method has industrial applicability.

What is claimed is:

1. A method for separating p-xylene, comprising the steps of separating and recovering only p-xylene from a p-xylene-containing raw material mixture at a high-temperature and under a high-pressure using a zeolite membrane as a separating membrane, wherein a p-xylene partial pressure at a raw material side of said separating membrane is controlled at a pressure higher than an inflection point of a p-xylene adsorption curve and a p-xylene partial pressure at a recovery side of said separating membrane is controlled at a pressure which is not higher than the inflection point of the p-xylene adsorption curve at said high-temperature, such that a p-xylene permeation rate is at least 200 μmol/(m²·sec) when said p-xylene partial pressure on said recovery side is 20 kPa or less.

2. A method for separating p-xylene, comprising the steps of separating and recovering only p-xylene from a p-xylene-containing raw material mixture under high-temperature and high-pressure conditions using a zeolite membrane as a separating membrane, wherein said separation step is conducted at a temperature of 200° C. or higher, a p-xylene partial pressure at a raw material side of said separating membrane is kept at 100 kPa or higher, and a p-xylene partial pressure at a recovery side of said separating membrane is controlled at 20 kPa or lower, such that a p-xylene permeation rate is at least 200 μmol/(m²·sec).

3. The method for separating p-xylene according to claim 2, wherein said separation step is conducted at a temperature of 200° C. or higher, the p-xylene partial pressure at said raw material side of said separating membrane is kept at 100 kPa or higher, and the p-xylene partial pressure at said recovery side of said separating membrane is controlled at 20 kPa or lower.

4. The method for separating p-xylene according to claim 1, wherein said separating membrane comprises a MFI zeolite membrane.

5. The method for separating p-xylene according to claim 2, wherein said separating membrane comprises a MFI zeolite membrane.

6. The method for separating p-xylene according to claim 2, wherein said p-xylene partial pressure at said raw material side is 700 kPa, and wherein said separation step is conducted at a temperature of 400° C.

* * * * *

UNITED STATES PATENT AND TRADEMARK OFFICE
CERTIFICATE OF CORRECTION

PATENT NO.   : 6,646,177 B2
DATED        : November 11, 2003
INVENTOR(S)  : Tomonori Takahashi, Hitoshi Sakai and Naoyuki Ogawa It is certified that error appears in the above-identified patent and that said Letters Patent is hereby corrected as shown below:

Column 7,
Line 36, please change "amount J. (wherein J is a p-xylene permeation amount; K is" to
-- amount J.
(1)     J=K(Am-Ap)
(wherein J is a p-xylene permeation amount; K is --

Column 6,
Line 22, please change "J=K(Am-Ap)     (1)" to
-- (1)     J=K(Am-Ap) --

Signed and Sealed this

Twenty-third Day of March, 2004

JON W. DUDAS
*Acting Director of the United States Patent and Trademark Office*